(12) United States Patent
Kunert et al.

(10) Patent No.: US 6,297,181 B1
(45) Date of Patent: Oct. 2, 2001

(54) BARIUM-FREE, X-RAY-OPAQUE DENTAL GLASS AND DENTAL GLASS/POLYMER COMPOSITE, AND THE USE THEREOF

(75) Inventors: Christian Kunert, Mainz; Susanne Kessler; Hartmut Paschke, both of Ergolding; Alwin Weitzel; Ute Wolfel, both of Maninz, all of (DE)

(73) Assignee: Schott Glas, Mainz (DE)

( * ) Notice: Subject to any disclaimer, the term of this patent is extended or adjusted under 35 U.S.C. 154(b) by 0 days.

(21) Appl. No.: 09/427,590

(22) Filed: Oct. 27, 1999

(30) Foreign Application Priority Data

Oct. 27, 1998 (DE) ................................ 198 49 388

(51) Int. Cl.[7] .......................... C03C 3/062; C03C 3/066; C03C 3/085; C03C 3/087; A61K 6/027

(52) U.S. Cl. ................. 501/57; 501/59; 501/63; 501/64; 501/67; 501/69; 501/70; 501/73; 501/79; 523/117; 106/35; 433/228.1

(58) Field of Search ................. 501/57, 59, 63, 501/64, 67, 69, 70, 72, 73, 79; 523/117; 106/35; 433/228.1

(56) References Cited

U.S. PATENT DOCUMENTS

| | | | |
|---|---|---|---|
| 2,537,955 | * | 1/1951 | Baldwin ................... 501/79 |
| 3,971,754 | | 7/1976 | Jurecic . |
| 4,215,033 | | 7/1980 | Bowen . |
| 4,358,549 | | 11/1982 | Randklev . |
| 4,376,835 | * | 3/1983 | Schmitt et al. ............. 501/39 |
| 4,747,876 | * | 5/1988 | Hakamatsuka et al. ........ 501/57 |
| 4,775,592 | | 10/1988 | Akahane et al. . |
| 4,799,887 | * | 1/1989 | Hakamatsuka et al. . |
| 4,814,362 | | 3/1989 | Billington et al. . |
| 5,215,459 | | 6/1993 | Ney et al. . |
| 5,520,922 | * | 5/1996 | Gasser et al. ............. 424/422 |
| 5,641,347 | | 6/1997 | Grabowski et al. . |
| 5,679,710 | | 10/1997 | Davy et al. . |

FOREIGN PATENT DOCUMENTS

| | | | |
|---|---|---|---|
| 3248357 | | 7/1984 | (DE) . |
| 34 21 155 | * | 12/1985 | (DE) . |
| 4023744 | | 2/1992 | (DE) . |
| 3788816 | | 5/1994 | (DE) . |
| 4323143 | | 12/1994 | (DE) . |
| 4443173 | | 7/1996 | (DE) . |
| 4443173 | | 4/1997 | (DE) . |
| 0241277 | | 10/1987 | (EP) . |
| 0716049 | | 6/1996 | (EP) . |
| 2202221 | | 9/1988 | (GB) . |
| 61-215234 | | 9/1986 | (JP) . |
| 04-092836 | * | 3/1992 | (JP) . |
| 5-331017 | | 12/1993 | (JP) . |
| 6-39031 | | 2/1994 | (JP) . |

* cited by examiner

*Primary Examiner*—David R Sample
(74) *Attorney, Agent, or Firm*—Millen, White, Zelano & Branigan, P.C.

(57) ABSTRACT

The invention relates to a barium-free, X-ray-opaque dental glass, to a dental glass/polymer composite comprising the glass, and to the use thereof as dental filling, where the dental glass has the following composition (in % by weight): $SiO_2$ 20–45, $Al_2O_3$ 5–35, $B_2O_3$ 1–10, $Na_2O$ 1–10, $K_2O$ 0–8, $Cs_2O$ 0–8, sum all alkali metal oxides 1–15, CaO 0–8, SrO 0–27, ZnO 2–20, $ZrO_2$ 2–10, $P_2O_5$ 0–10, $La_2O_3$ 0–10, F 2–20, the total content of $B_2O_3$, ZnO, $ZrO_2$ and $La_2O_3$ is >20% by weight, and the refractive index $n_d$ of the dental glass is in the range from 1.47 to 1.70.

26 Claims, No Drawings

BARIUM-FREE, X-RAY-OPAQUE DENTAL GLASS AND DENTAL GLASS/POLYMER COMPOSITE, AND THE USE THEREOF

FIELD OF THE INVENTION

The invention relates to a barium-free, X-ray-opaque dental glass, to a dental glass/polymer composite comprising the glass, and to the use thereof.

BACKGROUND OF THE INVENTION

For dental fillings, use is increasingly being made of dental glass/polymer composites in order to avoid possible side-effects of amalgam fillings and in order to achieve a better aesthetic impression. Dental glass/polymer composites generally consist of an inorganic component and an organic polymer binder. The inorganic component consists predominantly of glass powder. Besides the powder properties necessary for good filling, the glass powder used also has to meet certain requirements regarding the physical and chemical properties of the glass to be used for the powder.

The refractive index of the glass powder must be matched as closely as possible to that of the synthetic resin matrix used in order to imitate the partially transparent appearance of natural tooth enamel and thus to meet the high aesthetic requirements.

Refractive index differences between glass and synthetic resin of greater than 0.05 result in undesirably high opacity of the dental glass/polymer composite and should therefore be avoided. In addition, the glass powder must have good processing properties and favourable setting behaviour during preparation of the composites and must ensure high strength after curing.

It is furthermore important that the thermal expansion of the dental glass/polymer composite in the area of use of the filling, i.e. at temperatures between 30° C. and 70° C., is matched to that of the tooth material in order to ensure that the filling has adequate thermal shock resistance. In particular the change between cold and hot foods entails the risk here of the filling loosening due to such thermal shock stressing and of a gap thus forming between the filling and the tooth, representing a preferential point of attack for secondary caries. It is usual for the glass to have the lowest possible expansion coefficient, since this allows compensation for the relatively high thermal expansion of the synthetic resin binder.

The X-ray opacity of dental glasses or materials is, in accordance with DIN ISO 4049, quoted relative to the X-ray absorption of aluminium as the aluminium equivalent thickness (AlET). The AlET is the thickness of an aluminium sample which produces the same absorption as a 2 mm thick sample of the material to be tested. An AlET of 4 mm thus means that a glass plate with a thickness of 2 mm produces the same X-ray attenuation as an aluminium plate with a thickness of 4 mm. X-ray-opaque dental glasses are required to have an AlET of at least 4 mm. This ensures sufficiently good differentiation capacity between filling and tooth material on X-ray pictures when used as dental filling. Gaps which have occurred and caries can be recognised well.

Furthermore, good chemical resistance of the glass powder to water, acids and caustic lyes must contribute to a long life of the dental filling. Owing to possible toxic side effects, the use of barium constituents in the glass should be avoided, although these constituents produce good X-ray opacity. The use of lead-containing constituents is likewise undesired from toxic points of view.

DE 32 48 357 A1 describes a pulverulent dental material based on calcium aluminium fluorosilicate glasses (a) and metals (b) usual for dental purposes and further components, which is characterized in that it contains at least some of (a) as a sintered mixture with (b). The powders of (a) used consist of (% by weight, calculated as oxides) $SiO_2$ 20–60, $Al_2O_3$ 10–50, CaO 1–40, F 1–40, $Na_2O$ 0–10, $P_2O_5$ 0–10 and a total of 0–20% by weight, calculated as oxides, of B, Bi, Zn, Mg, Sn, Ti, Zr, La or other trivalent lanthanide oxides, K, W and Ge.

U.S. Pat. No. 5,215,459 relates to the use of glass ionomer cements for controlled tissue regeneration. The composition ranges quoted for the glass powder correspond to those given in DE 32 48 357 A1 with in addition SrO as an optional constituent in an amount of 0–40% by weight, where CaO and/or SrO are at least 1% by weight. In order to make the glass X-ray-visible, from 10 to 20% by weight of $La_2O_3$ can be added.

The glasses described in the abovementioned specifications have a relatively low total content of $B_2O_3$, ZnO, $ZrO_2$ and $La_2O_3$ ($\leq 20\%$ by weight).

U.S. Pat. No. 4,775,592 describes a fluoroaluminosilicate glass for use as dental glass ionomer cement whose surface has been post-treated with a metal fluoride or a fluoro complex salt. The complex post-treatment here serves to achieve the requisite processing properties and a high compressive strength of the cement. The composition of the fluoroaluminosilicate glass powder can be in a broad composition range. It is prepared by melting the components (in % by weight) $SiO_2$ 25–50, $Al_2O_3$ 15–40, F 10–40 and phosphate 0–20. F here can be introduced as the fluoride of Zn, Al, Y, La, Zr, alkali metals and alkaline earth metals, and phosphate as the phosphate of alkali metals, alkaline earth metals, Zn, Al, Y, La and Zr. Oxides of Y, La, Zn, Ti, Zr and alkaline earth metals can also be introduced into the glass. JP 61-215234 A claims a glass composition for use as glass ionomer cement, suitable as dental cement. A broad composition range consisting of a multiplicity of possible components is claimed. Nevertheless, the specification only allows the production of glasses having a relatively low refractive index in an additionally narrow range of from 1.46 to 1.60. Glasses having refractive indices in the range >1.60 which is favourable for novel dental materials are not described. A Ba content of up to 35% of weight is possible. The Ba content of 20.31 and 3.92% by weight given in two examples is problematic for toxicological reasons and does not meet the requirements of modern dental glasses.

A striking feature in this specification and in U.S. Pat. No. 4,775,592 is the high claimed F content of from 10 to 40% by weight and the optional content of $B^{3+}$ and $P^{5+}$ of from 0 to 8% by weight each (JP 61-215234 A) or phosphate of from 0 to 20% by weight (U.S. Pat. No. 4,775,592). The production of a non-opacified dental glass having a high F content without the requisite presence of $B^{3+}$ and/or $P^{5+}$ is difficult.

U.S. Pat. No. 3,971,754 describes the production of a dental filling material using a barium-, zinc- and zirconium-free glass which, in order to produce X-ray opacity, contains oxides and carbonates of lanthanum, hafnium, strontium or tantalum in the range from 5 to 60% by weight.

JP 6-39031 A describes zinc-free, X-ray-opaque implant materials based on calcium apatite and strontium apatite glass ceramics. In the compositions described, the X-ray-absorbent component employed in virtually all cases is exclusively SrO; only in 2 examples is up to 5% by weight of $ZrO_2$ used. Fluxing agents, such as $Na_2O$ or $B_2O_3$, are present in at most very small amounts (maximum 0.5% by weight).

JP 5-331017 A describes zinc- and zirconium-free glass powders for dental cements whose X-ray-absorbing action is based on the use of SrO and $La_2O_3$ (up to 20% by weight).

DE 3788816 T2 describes a process for the preparation of radio-opaque, crosslinked poly(carboxylic acid) dental cement containing a fluorine-containing, zinc- and zirconium-free glass powder. The requisite X-ray absorption is produced by addition of from 5 to 35% by weight of SrO.

U.S. Pat No. 4,215,033 claims a dental resin composite consisting of a resin and a non-toxic, alkali metal- and fluoride-free filler, where the filler consists of a two-phase boroaluminosilicate glass and one phase is partly removed again. The glass can contain additions of SrO, CaO and ZnO or $SrO/ZrO_2$.

DE 44 43 173 C2 likewise claims a barium-free dental glass with a high silicon content (from 50 to 75% by weight of $SiO_2$) and good X-ray absorption.

Furthermore, DE 43 23 143 C1 discloses a barium-, zinc- and zirconium-free dental glass having high X-ray absorption and a refractive index $n_d \leq 1.56$ which has a composition, in % by weight, based on oxide, of $SiO_2$ 45–65, $B_2O_3$ 5–20, $Al_2O_3$ 5–20, CaO 0–10, SrO 15–35 and $F_2$—O 0–2. The good X-ray opacity is achieved here through a relatively high content of SrO.

The object of the invention is to find a barium-free, X-ray-opaque dental glass for use in dental glass/polymer composites and to provide a dental glass/polymer composite comprising such a dental glass. The dental glass and the dental glass/polymer composite should be inexpensive, but nevertheless high-quality and tolerated by the body, and should be suitable for passive and active tooth protection and should have excellent properties regarding processing, setting behaviour and strength.

The refractive index $n_d$ of the dental glass should be matched to the available dental polymers, particularly to those having a refractive index $n_d > 1.60$, and so meet the aesthetic demands for a natural appearance made of a dental glass/polymer composite.

SUMMARY OF THE INVENTION

To achieve the object relating to dental glass, there is provided a barium-free, X-ray-opaque dental glass, characterized by a composition (in % by weight) of:

| | |
|---|---|
| $SiO_2$ | 20–45 |
| $Al_2O_3$ | 5–35 |
| $B_2O_3$ | 0–10 |
| $Na_2O$ | 1–10 |
| $K_2O$ | 0–8 |
| $Cs_2O$ | 0–8 |
| $Na_2O + K_2O + Cs_2O$ | 1–15 |
| CaO | 0–8 |
| SrO | 0–27 |
| ZnO | 2–20 |
| $ZrO_2$ | 2–10 |
| $P_2O_5$ | 0–10 |
| $La_2O_3$ | 0–10 |
| F | 2–20 |
| $B_2O_3 + ZnO + ZrO_2 + La_2O_3$ | >20 | and a refractive index $n_d$ of from 1.47 to 1.70.

To achieve the object of a dental glass/polymer composite, there is provided a composite comprising a dental polymer and the above described dental glass.

The dental glass according to the invention achieves the properties of barium-containing dental glasses with respect to the requisite X-ray absorption without use of barium compounds or other substances which are suspect from a health point of view.

In contrast to conventional dental glasses, the requisite X-ray opacity is not produced by only one component alone, but instead by a combination of various X-ray-absorbent elements, whose actions are preferably mutually complementary since they absorb different regions of the radiation from the X-ray tubes.

The minimum content of ZnO in the glasses according to the invention enables the utilization of the bacteriostatic action of $Zn^{2+}$, in particular in the critical interface region between filling and surrounding tooth.

The refractive index $n_d$ of the dental glass can be varied over a broad range of from 1.47 to 1.70, the further requirements mentioned being satisfied over the entire range.

The refractive indices $n_d$ of the dental glasses correspond to those of conventional dental polymers that are available. For a certain dental polymer having a specified refractive index $n_d$, in particular also for relatively new high-refraction synthetic resins having $n_d > 1.6$, as described, for example, in U.S. Pat. No. 5,679,710, a dental glass having a matching refractive index is provided. This facilitates an appearance of the dental glass/polymer composite which corresponds to natural tooth enamel.

The glass contains 20–45% by weight of $SiO_2$ as glass-forming constituent. At lower contents, the tendency towards crystallization increases impermissably, meaning that clear glasses which are suitable for the desired application cannot be obtained. $SiO_2$ contents of greater than 45% by weight result in disadvantageously high melting temperatures, while at the same time the high X-ray opacity and the minimum fluoride content cannot be achieved.

$Al_2O_3$ is employed in the range from 5 to 35% by weight and $P_2O_5$ in the range from 0 to 10% by weight. The minimum content of $Al_2O_3$ is necessary in order to create a network with suitable structural units which enable the incorporation of fluoride to the requisite extent and thus the production of clear glasses. In particular at high fluoride contents, $P_2O_5$ is preferably also employed in addition. $Al_2O_3$ contents higher than 35% by weight result in disadvantageously high melting temperatures, while $P_2O_5$ contents of greater than 10% by weight result in a high separation tendency of the glasses and inadequate chemical resistance for further processing of the glasses and later use.

1–10% by weight of $Na_2O$ are employed in the glasses according to the invention as fluxing agent for lowering the melting temperature. The same purpose is achieved by $K_2O$ and $Cs_2O$, which can optionally additionally be employed, where the total alkali metal content in the glasses should not exceed 15% by weight in order to ensure adequate chemical and mechanical resistance. The use of $K_2O$ and $Cs_2O$ is particularly advisable if the requirement for inexpensive raw materials reduces in importance in order to achieve particularly high X-ray opacity at the same time as a high refractive index. However, the content should be limited to a maximum of 8% by weight each.

$B_2O_3$, similarly to the alkali metals, can be employed as fluxing agent in contents of up to 10% are weight. Besides the lowering action on the melting temperature, the use of $B_2O_3$ simultaneously results in an improvement in the crystallization stability of the glasses, meaning that clear, non-crystallizing glasses can be obtained even at relatively high fluoride contents. Higher concentrations than 10% by weight are not advisable since otherwise the chemical resistance drops.

ZnO is employed in the range between 2 and 20% by weight. At contents below 2% by weight, the requisite bacteriostatic action of the dental materials produced using the glasses according to the invention is no longer guaranteed. Higher contents than 20% by weight result in impaired chemical resistance. In addition, the solubility limit for ZnO for this glass system is then reached, resulting in crystallization problems. Furthermore, the addition of ZnO has a favourable effect on the setting behaviour.

Together with the above ZnO content, a $ZrO_2$ content of between 2 and 10% by weight ensures adequate X-ray absorption of the glasses according to the invention. A minimum content of 2% by weight in addition guarantees the desired chemical resistance; the mechanical properties, and in particular the tensile and compressive strength, are improved here, while with $ZrO_2$ contents above 10% by weight, the refractive index $n_d$ cannot be set in the desired range between 1.47 and 1.70 and at the same time the melting temperatures and in particular the crystallization tendency rise in an undesired manner.

In particular at low ZnO and $ZrO_2$ contents, the addition of up to 27% are weight of SrO is advisable for high X-ray opacity. The addition of SrO affects the refractive index and has a favourable effect on the melting properties and the setting behaviour. However, SrO contents of greater than 27% by weight result in increased crystallization and should be avoided. In particular in the case of SrO-free glasses, it is preferred to promote the desired setting behaviour by addition of up to 8% by weight of CaO. Addition of up to 10% by weight of $La_2O_3$ allows the requisite high X-ray absorption to be established particularly well. The characteristic X-ray absorption of ZnO, $ZrO_2$ and SrO is excellently supplemented in particular by the characteristic X-ray absorption of $La_2O_3$. This gives sufficiently high X-ray absorption over the entire energy range of the X-rays used for medical purposes.

In order to satisfy the demands made of dental glasses, the total content of the components $B_2O_3$, ZnO, $ZrO_2$ and $La_2O_3$ must be at least greater than 20% by weight.

Fluoride, employed as cryolite ($Na_3AlF_6$), $AlF_3$, $SrF_2$ or as fluoride of the other elements employed, also serves, in the range between 2 and 20% by weight, besides achieving a low refractive index $n_d$, as desired fluoride depot in the dental material, which releases fluoride to the surrounding tooth material over the course of time. In addition, the production of clear glasses is facilitated. This requires a minimum content of 2% by weight. Contents above 20% by weight should be avoided, since then the separation and crystallization tendency of the glasses during production increases drastically. In addition, considerable losses of fluoride in the melt can then be expected, which requires considerably increased personnel protection measures and increased effort in avoiding environmentally damaging vapours. The use of cryolite as fluoride raw material takes into account the requirement for using the cheapest possible raw materials for production.

The refractive index of the dental glass according to the invention can be set in the range from 1.47 to 1.70. In order that the appearance of the dental glass/polymer composites approaches that of natural tooth enamel, the refractive indices of dental glass and dental polymer are matched. Dental glasses according to the invention having a refractive index >1.60 are particularly suitable for the use of promising high-refraction synthetic resins, as described in U.S. Pat. No. 5,679,710.

Refractive indices in the range from 1.47 to 1.59 can be established by means of a dental glass having the composition (in % by weight) $SiO_2$ 20–45, $Al_2O_3$ 7–35, $B_2O_3$ 0.5–10, $Na_2O$ 2–10, $K_2O$ 0–8, $Cs_2O$ 0–8, sum of the alkali metal oxides 2–10, CaO 0–5, SrO 0–25, ZnO 2–15, $ZrO_2$ 2–6, $P_2O_5$ 2–10, $La_2O_3$ 0–5 and F 7–20. The total content of $B_2O_3$, ZnO, $ZrO_2$ and $La_2O_3$ is >20% by weight.

Refractive indices in the range from 1.49 to 1.57 can be established by means of a dental glass having the composition (in % by weight) $SiO_2$ 20–44, $Al_2O_3$ 12–22, $B_2O_3$ 5–10, $Na_2O$ 2–8, CaO 0–4, SrO 0–18.5, ZnO 3–15, $ZrO_2$ 3–6, $P_2O_5$ 4–10, $La_2O_3$ 0–4 and F 10–20. The total content of $B_2O_3$, ZnO, $ZrO_2$ and $La_2O_3$ is >20% by weight.

Refractive indices in the range from 1.59 to 1.70 can be established by means of a dental glass having the composition (in % by weight) $SiO_2$ 20–30, $Al_2O_3$ 5–25, $B_2O_3$ 0–10, $Na_2O$ 3–10, $K_2O$ 0–8, $Cs_2O$ 0–8, sum of the alkali metal oxides 3–15, CaO 0–8, SrO 0–25, ZnO 2–20, $ZrO_2$ 2–10, $P_2O_5$ 0–10, $La_2O_3$ 0–10 and F 2–10. The total content of $B_2O_3$, ZnO, $ZrO_2$ and $La_2O_3$ is >20% by weight. These dental glasses are distinguished by particularly good X-ray opacity.

In particular for high-refraction dental polymers having a refractive index $n_d$>1.60, the dental glasses according to the invention make available for the first time barium-free, X-ray-opaque filling glasses of matched refractive index.

Refractive indices in the range from 1.59 to 1.67 can be established by means of a dental glass having the composition (in % by weight) $SiO_2$ 20–30, $Al_2O_3$ 5–25, $B_2O_3$ 1–10, $Na_2O$ 3–10, $K_2O$ 0–8, $Cs_2O$ 0–8, sum of the alkali metal oxides 5–15, CaO 0–5, SrO 10–25, ZnO 8–20, $ZrO_2$ 4–10, $P_2O_5$ 2–10, $La_2O_3$ 3–10 and F 2–7. The total content of $B_2O_3$, ZnO, $ZrO_2$ and $La_2O_3$ is >20% by weight.

Refractive indices in the range from 1.59 to 1.66 can be established by means of a dental glass having the composition (in % by weight) $SiO_2$ 20–30, $Al_2O_3$ 5–15, $B_2O_3$ 2–5, $Na_2O$ 3–7, $K_2O$ 0–5, $Cs_2O$ 0–5, sum of the alkali metal oxides 5–13, CaO 0–5, SrO 15–24, ZnO 10–15, $ZrO_2$ 4–9, $P_2O_5$ 2–5, $La_2O_3$ 3–8 and F 2–5. The total content of $B_2O_3$, ZnO, $ZrO_2$ and $La_2O_3$ is >20% by weight.

Besides SrO, $ZrO_2$, ZnO and $La_2O_3$, the glasses according to invention can contain, as further X-ray-absorbent components, further oxides from the groups ($SC_2O_3$, $Y_2O_3$, $Nb_2O_5$, $Gd_2O_3$, $Yb_2O_3$) and ($HfO_2$, $Ta_2O_5$, $WO_3$) in an amount of up to 10% by weight per group. These components are preferably not employed for the production of inexpensive glasses having low refractive indices. In these cases, the X-ray opacity is ensured by a combination of ZnO, $ZrO_2$, SrO and optionally $La_2O_3$.

For dental practice, good recognizability of the filling in the X-ray picture is of high importance. The dental glasses according to invention have aluminium equivalent thicknesses of least 4 mm and thus satisfy the requisite properties for use in dental restoration.

Owing to its composition of customary compounds in glass production, the dental glass can be produced inexpensively. Through the advantageous combination of these compounds, a dental glass of high quality with respect to strength, setting behaviour and processing properties which is tolerated by the body has been found.

A dental glass/polymer composite according to the invention and a dental glass suitable therefor is distinguished not only by the excellent use for passive dental protection, for example in the form of dental fillings, but, owing to its composition, particularly through the use of the bacteriostatic components zinc and fluoride, can participate actively in preventative dental protection.

The glasses according to the invention are produced as follows:

The raw materials, preferably carbonates and fluorides, are weighed out and then mixed thoroughly. The glass batch is melted at about 1400–1540° C. and homogenized well. The temperature during casting is 1280–1460° C. The casting is preferably carried out onto water-cooled steel plates or rollers. The clear glass plates having thicknesses of up to 2 mm can subsequently easily be ground up with known agents to give glass powders for dental applications. A melt example for the production of a dental glass corresponding to Example 1.4 is shown in Table 3.

After its production, the glass is converted in a manner known per se, for example by grinding and optionally sieving, into a glass powder which has the mean particle size of $\leq 10 \mu m$, in particular from 0.5 to 5 $\mu m$, preferably from 0.7 to 1.5 $\mu m$, usual for dental purposes. The particle size of the powder plays an important role; it affects the ability of the composites to be polished and the abrasion and mechanical strength. In order to achieve good mechanical properties, a particle size distribution which is not too narrow is usually favourable, as achieved, for example, by conventional grinding and sieving out of the coarse components. A maximum particle size of 40 $\mu m$, preferably 20 $\mu m$, in particular 10 $\mu m$, should not be exceeded. In this form, the glass powder is particularly suitable for use as filler for dental composites used as dental fillings.

It is frequently usual to silanize the dental glass powders, silanization being well known per se and for this application. Silanization makes it easier to achieve a high degree of filling in the composite and has a favourable effect on the mechanical properties of the composite.

A dental glass/polymer composite according to the invention consists of conventional dental polymers and a dental glass powder according to the invention.

The refractive index $n_d$ of the dental glass preferably corresponds to that of the dental polymer within 0.05,. the refractive index $n_d$ of the dental polymer preferably being >1.60.

In order to prepare dental composites which can be used as dental fillings, the glass powder is mixed with curable synthetic resins usual in dental medicine. The synthetic resins used are predominantly UV-curable resins based on acrylate, methacrylate, 2,2-bis[4-(3-methacryloxy-2-hydroxypropoxy)phenyl]propane (bis-GMA), urethane methacrylate, alkanediol dimethacrylate or cyanoacrylate. The glass powder used for the filling is present in the finished synthetic resin pastes in proportions by weight of up to 80% by weight, where the glass powder content should be selected as high as possible for strength reasons.

Table 1 contains 5 working examples and properties (refractive index $n_d$, aluminium equivalent thickness AlET) in the composition range in which dental glasses having low refractive indices are found, and Table 2 contains a further 5 examples with high refractive indices.

TABLE 1

Examples of low-refraction glasses (composition in % by weight)

| Example | 1.1 | 1.2 | 1.3 | 1.4 | 1.5 |
|---|---|---|---|---|---|
| $SiO_2$ | 38 | 20 | 25 | 23 | 30 |
| $Al_2O_3$ | 12 | 12 | 15 | 12 | 12 |
| $B_2O_3$ | 10 | 10 | 10 | 10 | 5 |
| $Na_2O$ | 2 | 2 | 7 | 7 | 3 |
| SrO | — | 10 | — | 10 | — |
| ZnO | 6 | 15 | 15 | 6 | 15 |
| $ZrO_2$ | 3 | 3 | 6 | 3 | 6 |
| $P_2O_5$ | 5 | 10 | 5 | 10 | 10 |
| $La_2O_3$ | 4 | 2 | 2 | 4 | 4 |
| F | 20 | 16 | 15 | 15 | 15 |

TABLE 1-continued

Examples of low-refraction glasses (composition in % by weight)

| Example | 1.1 | 1.2 | 1.3 | 1.4 | 1.5 |
|---|---|---|---|---|---|
| $B_2O_3$ + ZnO + $ZrO_2$ + $La_2O_3$ | 23 | 30 | 33 | 23 | 30 |
| $n_d$ | 1.514 | 1.569 | 1.530 | 1.535 | 1.565 |
| AlET [mm] | 6.3 | 8.1 | 4.6 | 7.3 | 7.0 |

TABLE 2

Examples of high-refraction glasses (composition in % by weight)

| Example | 2.1 | 2.2 | 2.3 | 2.4 | 2.5 |
|---|---|---|---|---|---|
| $SiO_2$ | 30 | 25 | 30 | 22 | 20 |
| $Al_2O_3$ | 5 | 10 | 7 | 13 | 10 |
| $B_2O_3$ | 5 | 2 | 5 | 2 | 2 |
| $Na_2O$ | 5 | 7 | 6 | 2 | 5 |
| $K_2O$ | — | — | — | 2 | 5 |
| $Cs_2O$ | — | 3 | — | 5 | 3 |
| $Na_2O$ + $K_2O$ + $Cs_2O$ | 5 | 10 | 6 | 9 | 13 |
| CaO | 5 | — | — | — | 5 |
| SrO | 24 | 15 | 23 | 20 | 15 |
| ZnO | 10 | 15 | 10 | 15 | 14 |
| $ZrO_2$ | 8 | 8 | 4 | 7 | 9 |
| $P_2O_5$ | — | 4 | 4 | 3 | 2 |
| $La_2O_3$ | 3 | 6 | 8 | 6 | 8 |
| F | 5 | 5 | 3 | 3 | 2 |
| $B_2O_3$ + ZnO + $ZrO_2$ + $La_2O_3$ | 26 | 31 | 27 | 30 | 33 |
| $n_d$ | 1.608 | 1.601 | 1.598 | 1.634 | 1.656 |
| AlET [mm] | 11.4 | 11.3 | 11.3 | 12.3 | 11.9 |

TABLE 3

Melt example for 100 kg of calculated dental glass (corresponding to Table 1, Example 1.4)

| Component | % by weight | Raw material | Amount/kg |
|---|---|---|---|
| $SiO_2$ | 23.0 | $SiO_2$ | 23.01 |
| $Al_2O_3$ | 12.0 | Al$(OH)_3$ | 4.57 |
| $Na_2O$ | 7.0 | $Na_3AlF_6$ | 15.81 |
| $P_2O_5$ | 10.0 | Al$(PO_3)_3$ | 12.53 |
| $B_2O_3$ | 10.0 | $H_3BO_3$ | 17.77 |
| SrO | 10.0 | $SrF_2$ | 12.50 |
| ZnO | 6.0 | ZnO | 6.01 |
| $ZrO_2$ | 3.0 | $ZrO_2$ | 3.06 |
| $La_2O_3$ | 4.0 | $La_2O_3$ | 4.01 |
| F | 15.0 | $AlF_3$ | 4.49 |
| Sum | 100.0 |  | 103.76 |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding German application 19849388.6, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Barium-free, X-ray-opaque dental glass, characterized by a composition (in % by weight) of the following components:

| | |
|---|---|
| $SiO_2$ | 20–45 |
| $Al_2O_3$ | 5–35 |
| $B_2O_3$ | 0–10 |
| $Na_2O$ | 1–10 |
| $K_2O$ | 0–8 |
| $Cs_2O$ | –8 |
| $Na_2O + K_2O + Cs_2O$ | 1–15 |
| CaO | 0–8 |
| SrO | 0–27 |
| ZnO | 2–20 |
| $ZrO_2$ | 2–10 |
| $P_2O_5$ | 0–10 |
| $La_2O_3$ | 0 to less than 10 |
| F | 11 2–20 |
| $B_2O_3 + ZnO + ZrO_2 + La_2O_3$ | >20 | and a refractive index $n_d$ of from 1.47 to 1.70, and an aluminum equivalent thickness of at least 4 mm.

2. Dental glass according to claim 1, characterized by a composition (in % by weight) of:

| | |
|---|---|
| $SiO_2$ | 20–45 |
| $Al_2O_3$ | 7–35 |
| $B_2O_3$ | 0.5–10 |
| $Na_2O$ | 2–10 |
| $K_2O$ | 0–8 |
| $Cs_2O$ | 0–8 |
| $Na_2O + K_2O + Cs_2O$ | 2–10 |
| CaO | 0–5 |
| SrO | 0–25 |
| ZnO | 2–15 |
| $ZrO_2$ | 2–6 |
| $P_2O_5$ | 2–10 |
| $La_2O_3$ | 0–5 |
| F | 7–20 |
| $B_2O_3 + ZnO + ZrO_2 + La_2O_3$ | >20 | and a refractive index $n_d$ of from 1.47 to 1.59.

3. Dental glass according to claim 1, characterized by a composition (in % by weight) of:

| | |
|---|---|
| $SiO_2$ | 20–44 |
| $Al_2O_3$ | 12–22 |
| $B_2O_3$ | 5–10 |
| $Na_2O$ | 2–8 |
| CaO | 0–4 |
| SrO | 0–18.5 |
| ZnO | 3–15 |
| $ZrO_2$ | 3–6 |
| $P_2O_5$ | 4–10 |
| $La_2O_3$ | 0–4 |
| F | 10–20 |
| $B_2O_3 + ZnO + ZrO_2 + La_2O_3$ | >20 | and a refractive index $n_d$ of from 1.49 to 1.57.

4. Dental glass according to claim 1, characterized by a composition (in % by weight) of:

| | |
|---|---|
| $SiO_2$ | 20–30 |
| $Al_2O_3$ | 5–25 |
| $B_2O_3$ | 0–10 |
| $Na_2O$ | 3–10 |
| $K_2O$ | 0–8 |
| $Cs_2O$ | 0–8 |
| $Na_2O + K_2O + Cs_2O$ | 3–15 |
| CaO | 0–8 |
| SrO | 0–25 |
| ZnO | 2–20 |
| $ZrO_2$ | 2–10 |
| $P_2O_5$ | 0–10 |
| $La_2O_3$ | 0 to less than 10 |
| F | 2–10 |
| $B_2O_3 + ZnO + ZrO_2 + La_2O_3$ | >20 | and a refractive index $n_d$ of from 1.59 to 1.70.

5. Dental glass according to claim 1 characterized by a composition (in % by weight) of

| | |
|---|---|
| $SiO_2$ | 20–30 |
| $Al_2O_3$ | 5–25 |
| $B_2O_3$ | 0–10 |
| $Na_2O$ | 3–10 |
| $K_2O$ | 0–8 |
| $Cs_2O$ | 0–8 |
| $Na_2O + K_2O + Cs_2O$ | 5–15 |
| CaO | 0–5 |
| SrO | 10–25 |
| ZnO | 8–20 |
| $ZrO_2$ | 4–10 |
| $P_2O_5$ | 2–10 |
| $La_2O_3$ | 0 to less than 10 |
| F | 2–7 |
| $B_2O_3 + ZnO + ZrO_2 + La_2O_3$ | >20 | and a refractive index of from 1.59 to 1.67.

6. Dental glass according to claim 1, characterized by a composition ( in % by weight) of:

| | |
|---|---|
| $SiO_2$ | 20–30 |
| $Al_2O_3$ | 5–15 |
| $B_2O_3$ | 2–5 |
| $Na_2O$ | 3–7 |
| $K_2O$ | 0–5 |
| $Cs_2O$ | 0–5 |
| $Na_2O + K_2O + Cs_2O$ | 5–13 |
| CaO | 0–5 |
| SrO | 15–24 |
| ZnO | 10–15 |
| $ZrO_2$ | 4–9 |
| $P_2O_5$ | 2–5 |
| $La_2O_3$ | 3–8 |
| F | 2–5 |
| $B_2O_3 + ZnO + ZrO_2 + La_2O_3$ | >20 | and a refractive index of from 1.59 to 1.66.

7. Dental glass according to claim 1, characterized by an additional content of up to 10% by weight of one or more oxides from the group consisting of $Sc_2O_3$, $Y_2O_3$, $Nb_2O_5$, $Gd_2O_3$ and $Yb_2O_3$, where the sum of these oxides is not greater than 10% by weight.

8. Dental glass according to claim 1, characterized by an additional content of up to 10% by weight of one or more oxides from the group consisting of $HfO_2$, $Ta_2O_5$ and $WO_3$, where the sum of these oxides is not greater than 10% by weight.

9. Dental glass according to claim 1, characterized in that the dental glass is in powder form having a mean particle size of $\leq 10$ μm.

10. A dental glass according to claim 9, having a mean particle size of 0.5 to 5 μm.

11. A dental glass according to claim 9, wherein all the components were melted together and the melt was ground to a powder.

12. Dental glass/polymer composite consisting essentially of a dental polymer and a dental glass according to claim 1.

13. Dental glass/polymer composite according to claim 12, characterized in that the dental polymer is a predominantly UV-curable resin based on acrylate, methacrylate, 2,2-bis[4-(3-methacryloxy-2-hydroxypropoxy)phenyl] propane (bis-GMA), urethane methacrylate, alkanediol dimethacrylate or cyanoacrylate.

14. Dental glass/polymer composite according to claim 12, characterized in that the refractive index $n_d$ of the dental glass corresponds to that of the dental polymer within 0.05.

15. Dental glass/polymer composite according to claim 14, characterized in that the refractive index $n_d$ of the dental polymer is >1.60.

16. Dental glass/polymer composite according to claim 12, characterized by a dental glass content of up to 80% by weight.

17. An article comprising a cured composite according to claim 12.

18. An article comprising a cured composite according to claim 13.

19. Dental glass/polymer composite consisting essentially of a dental polymer and a dental glass according to claim 2.

20. Dental glass/polymer composite consisting essentially of a dental polymer and a dental glass according to claim 3.

21. Dental glass/polymer composite consisting essentially of a dental polymer and a dental glass according to claim 4.

22. Dental glass/polymer composite consisting essentially of a dental polymer and a dental glass according to claim 5.

23. Dental glass/polymer composite consisting essentially of a dental polymer and a dental glass according to claim 6.

24. Dental glass/polymer composite consisting essentially of a dental polymer and a dental glass according to claim 7.

25. Dental glass/polymer composite consisting essentially of a dental polymer and a dental glass according to claim 8.

26. Dental glass/polymer composite consisting essentially of a dental polymer and a dental glass according to claim 9.

* * * * *

UNITED STATES PATENT AND TRADEMARK OFFICE
CERTIFICATE OF CORRECTION

PATENT NO.     : 6,297,181 B1
DATED          : October 2, 2001
INVENTOR(S)    : Kunert et al.

It is certified that error appears in the above-identified patent and that said Letters Patent is hereby corrected as shown below:

Column 9,
Line 12, reads "-8" should read -- 0-8 --
Line 18, reads "11 2-20" should read -- 2-20 --

Column 10,
Line 22, reads "0-10" should read -- 1-10 --
Line 30, reads "0 to less than 10" should read -- 3 to less than 10 --

Signed and Sealed this

Eighteenth Day of March, 2003

JAMES E. ROGAN
*Director of the United States Patent and Trademark Office*